(12) United States Patent
Barwood et al.

(10) Patent No.: US 8,932,354 B2
(45) Date of Patent: Jan. 13, 2015

(54) TENODESIS FIXATION METHOD

(76) Inventors: Shane Barwood, Victoria (AU); Farnaz L. Yassaee, Norwood, NJ (US)

( * ) Notice: Subject to any disclaimer, the term of this patent is extended or adjusted under 35 U.S.C. 154(b) by 141 days.

(21) Appl. No.: 12/763,201

(22) Filed: Apr. 19, 2010

(65) Prior Publication Data

US 2011/0106253 A1    May 5, 2011

(51) Int. Cl.
*A61F 2/08* (2006.01)
(52) U.S. Cl.
CPC ....... *A61F 2/0811* (2013.01); *A61F 2002/0858* (2013.01); *A61F 2002/0829* (2013.01); *A61F 2002/0888* (2013.01); *A61F 2/0805* (2013.01); *A61F 2002/0852* (2013.01)
USPC ..................................................... 623/13.14
(58) Field of Classification Search
USPC .............. 623/13.11–13.2; 606/232, 233, 300, 606/304, 321
See application file for complete search history.

(56) References Cited

U.S. PATENT DOCUMENTS

| | | | |
|---|---|---|---|
| 4,532,926 A | | 8/1985 | O'Holla |
| 4,784,126 A | | 11/1988 | Hourahane |
| 4,950,270 A | | 8/1990 | Bowman et al. |
| 5,037,422 A | * | 8/1991 | Hayhurst et al. ............ 606/232 |
| 5,062,843 A | | 11/1991 | Mahony, III |
| 5,100,417 A | * | 3/1992 | Cerier et al. ................. 606/139 |
| 5,102,421 A | | 4/1992 | Anspach, Jr. |
| 5,116,337 A | | 5/1992 | Johnson |
| 5,167,664 A | | 12/1992 | Hodorek |
| 5,176,682 A | * | 1/1993 | Chow .......................... 606/232 |
| 5,236,445 A | * | 8/1993 | Hayhurst et al. ............ 606/232 |
| 5,258,016 A | * | 11/1993 | DiPoto et al. ................ 606/232 |
| 5,268,001 A | * | 12/1993 | Nicholson et al. ........... 606/232 |
| 5,269,809 A | | 12/1993 | Hayhurst et al. |
| 5,282,802 A | | 2/1994 | Mahony, III |
| 5,354,300 A | | 10/1994 | Goble et al. |
| 5,370,662 A | * | 12/1994 | Stone et al. .................. 606/232 |
| 5,372,599 A | * | 12/1994 | Martins ......................... 606/75 |
| RE34,871 E | | 3/1995 | McGuire et al. |
| 5,409,486 A | | 4/1995 | Reese |
| 5,423,860 A | * | 6/1995 | Lizardi et al. ............... 606/232 |
| 5,472,452 A | * | 12/1995 | Trott ............................. 606/232 |

(Continued)

FOREIGN PATENT DOCUMENTS

EP    1006948    6/2000

OTHER PUBLICATIONS

Brown et al., "Endoscopic Anterior Cruciate Ligament Reconstruction Using Doubled Gracilis and Semitendinosus Tendons and Endobutton Femoral Fixation," Operative Techniques in Sports Medicine, Oct. 1999, pp. 201-213, vol. 7, No. 4.

(Continued)

*Primary Examiner* — Alvin Stewart
(74) *Attorney, Agent, or Firm* — Clayton, Howarth & Cannon, P.C.

(57) ABSTRACT

A tendon anchoring device may include an implant having a pair of spaced apart legs for straddling a tendon. A push rod removably attached to the implant may be utilized to guide and push a portion of the tendon into a pre-drilled bore in a bone. A fixation member may be slid along the push rod and threadably engage an inner surface of the pre-drilled bore to thereby anchor the tendon to the bone while a force is applied to the push rod. Once the fixation member has been installed, the push rod may be disengaged from the implant and removed from the bore. The implant may remain permanently straddled over the tendon inside of the bore.

62 Claims, 11 Drawing Sheets

(56) References Cited

U.S. PATENT DOCUMENTS

| | | | |
|---|---|---|---|
| 5,486,197 A * | 1/1996 | Le et al. | 606/232 |
| 5,496,326 A | 3/1996 | Johnson | |
| 5,545,180 A * | 8/1996 | Le et al. | 606/232 |
| 5,584,835 A * | 12/1996 | Greenfield | 606/232 |
| 5,601,557 A * | 2/1997 | Hayhurst | 606/232 |
| 5,632,748 A * | 5/1997 | Beck et al. | 606/89 |
| 5,643,320 A | 7/1997 | Lower et al. | |
| 5,645,589 A * | 7/1997 | Li | 606/60 |
| 5,647,874 A * | 7/1997 | Hayhurst | 606/232 |
| 5,674,224 A | 10/1997 | Howell et al. | |
| 5,681,352 A | 10/1997 | Clancy, III et al. | |
| 5,683,418 A | 11/1997 | Luscombe et al. | |
| 5,707,395 A * | 1/1998 | Li | 606/232 |
| 5,720,765 A | 2/1998 | Thal | |
| 5,725,529 A * | 3/1998 | Nicholson et al. | 606/232 |
| 5,728,136 A | 3/1998 | Thal | |
| 5,733,307 A * | 3/1998 | Dinsdale | 606/232 |
| 5,741,300 A | 4/1998 | Li | |
| 5,755,718 A | 5/1998 | Sklar | |
| 5,814,072 A | 9/1998 | Bonutti | |
| 5,860,978 A * | 1/1999 | McDevitt et al. | 606/232 |
| 5,871,504 A * | 2/1999 | Eaton et al. | 606/232 |
| 5,876,455 A | 3/1999 | Harwin | |
| 5,899,938 A | 5/1999 | Sklar et al. | |
| 5,906,632 A * | 5/1999 | Bolton | 606/232 |
| 5,911,721 A * | 6/1999 | Nicholson et al. | 606/326 |
| 5,916,216 A | 6/1999 | DeSatnick et al. | |
| RE36,289 E * | 8/1999 | Le et al. | 606/232 |
| 5,931,869 A | 8/1999 | Boucher et al. | |
| 5,935,129 A * | 8/1999 | McDevitt et al. | 606/232 |
| 5,957,953 A * | 9/1999 | DiPoto et al. | 606/232 |
| 5,961,520 A | 10/1999 | Beck, Jr. et al. | |
| 5,961,538 A * | 10/1999 | Pedlick et al. | 606/232 |
| 5,968,044 A | 10/1999 | Nicholson et al. | |
| 5,968,045 A | 10/1999 | Frazier | |
| 6,022,373 A * | 2/2000 | Li | 606/232 |
| 6,024,758 A * | 2/2000 | Thal | 606/232 |
| 6,045,574 A * | 4/2000 | Thal | 606/232 |
| 6,048,343 A | 4/2000 | Mathis et al. | |
| 6,099,530 A | 8/2000 | Simonian et al. | |
| 6,146,406 A * | 11/2000 | Shluzas et al. | 606/232 |
| 6,149,669 A * | 11/2000 | Li | 606/232 |
| 6,159,235 A * | 12/2000 | Kim | 606/232 |
| 6,264,694 B1 | 7/2001 | Weiler | |
| 6,290,711 B1 * | 9/2001 | Caspari et al. | 606/232 |
| 6,508,830 B2 * | 1/2003 | Steiner | 606/232 |
| 6,517,542 B1 * | 2/2003 | Papay et al. | 606/232 |
| 6,527,795 B1 * | 3/2003 | Lizardi | 606/232 |
| 6,599,289 B1 * | 7/2003 | Bojarski et al. | 606/60 |
| 6,635,073 B2 * | 10/2003 | Bonutti | 606/232 |
| 6,778,861 B1 * | 8/2004 | Liebrecht et al. | 607/116 |
| 6,916,321 B2 | 7/2005 | TenHuisen et al. | |
| 6,984,241 B2 | 1/2006 | Lubbers et al. | |
| 7,008,451 B2 * | 3/2006 | Justin et al. | 623/13.14 |
| 7,022,129 B2 * | 4/2006 | Overaker et al. | 606/232 |
| 7,141,066 B2 | 11/2006 | Steiner et al. | |
| 7,144,413 B2 * | 12/2006 | Wilford et al. | 606/232 |
| 7,172,595 B1 * | 2/2007 | Goble | 606/86 A |
| 7,201,773 B2 | 4/2007 | Steiner et al. | |
| 7,235,100 B2 * | 6/2007 | Martinek | 623/13.14 |
| 7,485,136 B2 * | 2/2009 | Chan | 606/321 |
| 7,637,949 B2 | 12/2009 | Hart | |
| 7,648,524 B2 * | 1/2010 | Zhang et al. | 606/323 |
| 7,651,528 B2 * | 1/2010 | Montgomery et al. | 623/13.14 |
| 7,837,731 B2 * | 11/2010 | Sklar | 623/13.14 |
| 7,857,817 B2 * | 12/2010 | Tallarida et al. | 606/96 |
| 7,867,251 B2 * | 1/2011 | Colleran et al. | 606/232 |
| 7,875,056 B2 * | 1/2011 | Jervis et al. | 606/232 |
| 7,951,198 B2 * | 5/2011 | Sucec et al. | 623/13.11 |
| 7,955,388 B2 * | 6/2011 | Jensen et al. | 623/13.14 |
| 8,066,713 B2 * | 11/2011 | DiMauro et al. | 606/94 |
| 8,110,001 B2 * | 2/2012 | Carter et al. | 623/13.14 |
| 8,128,658 B2 * | 3/2012 | Kaiser et al. | 606/232 |
| 2002/0007182 A1 * | 1/2002 | Kim | 606/53 |
| 2002/0040241 A1 * | 4/2002 | Jarvinen | 623/13.14 |
| 2002/0072797 A1 * | 6/2002 | Hays et al. | 623/13.14 |
| 2002/0161401 A1 * | 10/2002 | Steiner | 606/232 |
| 2002/0188298 A1 | 12/2002 | Chan | |
| 2003/0065332 A1 | 4/2003 | TenHuisen et al. | |
| 2003/0065361 A1 * | 4/2003 | Dreyfuss | 606/232 |
| 2003/0088251 A1 * | 5/2003 | Braun et al. | 606/73 |
| 2003/0088272 A1 * | 5/2003 | Smith | 606/232 |
| 2003/0105489 A1 * | 6/2003 | Eichhorn et al. | 606/232 |
| 2003/0105524 A1 * | 6/2003 | Paulos et al. | 623/13.14 |
| 2003/0171811 A1 | 9/2003 | Steiner et al. | |
| 2003/0216780 A1 * | 11/2003 | Fitts et al. | 606/232 |
| 2004/0111117 A1 * | 6/2004 | Colleran et al. | 606/232 |
| 2004/0133239 A1 * | 7/2004 | Singhatat | 606/232 |
| 2004/0153076 A1 * | 8/2004 | Singhatat et al. | 606/73 |
| 2004/0267361 A1 * | 12/2004 | Donnelly et al. | 623/13.14 |
| 2006/0095130 A1 * | 5/2006 | Caborn et al. | 623/13.14 |
| 2007/0055255 A1 * | 3/2007 | Siegel | 606/72 |
| 2007/0115805 A1 * | 5/2007 | Ge et al. | 370/218 |
| 2007/0162002 A1 | 7/2007 | Tornier | |
| 2007/0225805 A1 * | 9/2007 | Schmieding | 623/13.14 |
| 2008/0154314 A1 * | 6/2008 | McDevitt | 606/304 |
| 2008/0183290 A1 * | 7/2008 | Baird et al. | 623/13.14 |
| 2008/0208253 A1 * | 8/2008 | Dreyfuss et al. | 606/232 |
| 2008/0234730 A1 * | 9/2008 | Cotton et al. | 606/232 |
| 2008/0275469 A1 * | 11/2008 | Fanton et al. | 606/139 |
| 2008/0275554 A1 * | 11/2008 | Iannarone et al. | 623/13.14 |
| 2008/0306511 A1 * | 12/2008 | Cooper et al. | 606/232 |
| 2008/0319546 A1 * | 12/2008 | Bojarski et al. | 623/13.14 |
| 2009/0187216 A1 | 7/2009 | Schmieding et al. | |
| 2009/0192608 A1 | 7/2009 | Paulos | |
| 2009/0216326 A1 * | 8/2009 | Hirpara et al. | 623/13.14 |
| 2009/0254090 A1 | 10/2009 | Lizee | |
| 2009/0281581 A1 * | 11/2009 | Berg | 606/304 |
| 2009/0287259 A1 * | 11/2009 | Trenhaile et al. | 606/304 |
| 2009/0299386 A1 * | 12/2009 | Meridew | 606/151 |
| 2009/0312794 A1 * | 12/2009 | Nason et al. | 606/232 |
| 2009/0312795 A1 * | 12/2009 | Barbieri et al. | 606/232 |
| 2009/0318959 A1 * | 12/2009 | Burkhart | 606/228 |
| 2010/0016893 A1 * | 1/2010 | Fanton | 606/232 |
| 2010/0049258 A1 * | 2/2010 | Dougherty | 606/86 R |
| 2010/0063541 A1 * | 3/2010 | Brunelle et al. | 606/232 |
| 2010/0069958 A1 * | 3/2010 | Sullivan et al. | 606/232 |
| 2010/0145395 A1 * | 6/2010 | Graf et al. | 606/304 |
| 2010/0152773 A1 * | 6/2010 | Lunn et al. | 606/232 |
| 2010/0160962 A1 * | 6/2010 | Dreyfuss et al. | 606/228 |
| 2010/0161055 A1 * | 6/2010 | Donnelly et al. | 623/13.14 |
| 2010/0174369 A1 * | 7/2010 | Wang et al. | 623/13.14 |
| 2010/0179592 A1 * | 7/2010 | Martinek et al. | 606/232 |
| 2010/0185238 A1 * | 7/2010 | Cauldwell et al. | 606/232 |
| 2010/0217389 A1 * | 8/2010 | Cheng et al. | 623/13.14 |
| 2010/0241124 A1 * | 9/2010 | Housman et al. | 606/80 |
| 2010/0249833 A1 * | 9/2010 | Dreyfuss | 606/232 |
| 2010/0249930 A1 * | 9/2010 | Myers | 623/13.14 |
| 2010/0262184 A1 * | 10/2010 | Dreyfuss | 606/228 |
| 2010/0298888 A1 * | 11/2010 | Graf et al. | 606/304 |
| 2010/0331881 A1 * | 12/2010 | Hart | 606/232 |
| 2011/0004242 A1 * | 1/2011 | Stchur | 606/232 |
| 2011/0015675 A1 * | 1/2011 | Howard et al. | 606/232 |
| 2011/0054526 A1 * | 3/2011 | Stone et al. | 606/232 |
| 2011/0087283 A1 * | 4/2011 | Donnelly et al. | 606/232 |
| 2011/0106253 A1 * | 5/2011 | Barwood et al. | 623/13.14 |
| 2011/0112641 A1 * | 5/2011 | Justin et al. | 623/13.14 |
| 2011/0152930 A1 * | 6/2011 | Howe | 606/232 |
| 2011/0184516 A1 * | 7/2011 | Baird et al. | 623/13.14 |
| 2011/0184517 A1 * | 7/2011 | Baird et al. | 623/13.14 |
| 2011/0196490 A1 * | 8/2011 | Gadikota et al. | 623/13.14 |
| 2011/0251688 A1 * | 10/2011 | Sklar | 623/13.14 |
| 2011/0264140 A1 * | 10/2011 | Lizardi et al. | 606/232 |
| 2011/0276092 A1 * | 11/2011 | Dreyfuss | 606/232 |
| 2011/0282449 A1 * | 11/2011 | Montgomery et al. | 623/13.14 |
| 2011/0313453 A1 * | 12/2011 | Krumme et al. | 606/232 |
| 2012/0016415 A1 * | 1/2012 | Green et al. | 606/232 |
| 2012/0022588 A1 * | 1/2012 | Berg | 606/232 |
| 2012/0065677 A1 * | 3/2012 | West, Jr. | 606/232 |
| 2012/0071877 A1 * | 3/2012 | Frigg | 606/80 |
| 2012/0078298 A1 * | 3/2012 | Sklar | 606/232 |

(56) References Cited

U.S. PATENT DOCUMENTS

2012/0078300 A1* 3/2012 Mayer et al. ............... 606/232
2012/0083841 A1* 4/2012 DiMatteo et al. ........... 606/232

OTHER PUBLICATIONS

Drosdowech et al., "Arthroscopic Hamstring Anterior Cruciate Ligament Reconstruction with Endobutton Femoral Fixation," Operative Techniques in Sports Medicine, Jul. 1996, pp. 147-151, vol. 6, No. 3.
Fulkerson, "Central Quadriceps Free Tendon for Anterior Cruciate Ligament Reconstruction," Operative Techniques in Sports Medicine, Oct. 1999, pp. 195-200, vol. 7, No. 4.
Goitz et al., "Orthopedic Implants: A Guide to Radiographic Analysis," Current Problems in Diagnostic Radiology, Jul./Aug. 1996, pp. 113-168, vol. 25, No. 4.
Graf et al., "Endobutton Fixation of Hamstring Tendon Grafts," Operative Techniques in Sports Medicine, Oct. 1999, pp. 189-194, vol. 7, No. 4.
Howell et al., "Endoscopic Fixation of a Double-Looped Semitendinosus and Gracilis Anterior Cruciate Ligament Graft Using Bone Mulch Screw," Operative Techniques in Orthopaedics, Jul. 1996, pp. 152-160, vol. 6, No. 3.
Janis et al., "Spike Metallic Washer and Screw for Reattachment of the Achilles Tendon After Repair of a Distal Rupture," The Journal of Foot & Ankle Surgery, Jan./Feb. 2000, pp. 49-53, vol. 39, No. 1.
Kumar et al., "Posterolateral reconstruction of the knee: a tunnel technique for proximal fixation," The Knee, 1999, pp. 257-260, vol. 6.
Larson, "Anterior Cruciate Ligament Reconstruction with Hamstring Tendons," Operative Techniques in Orthopaedics, Jul. 1996, pp. 138-146, vol. 6, No. 3.
Leitman et al., "Quadriceps Tendon Anterior Cruciate Ligament Reconstruction Using the All-Inside Technique," Operative Techniques in Sports Medicine, Oct. 1999, pp. 179-188, vol. 7, No. 4.
MacGillivray et al., "Treatment of Acute and Chronic Injuries to the Posterolateral and Lateral Knee," Operative Techniques in Orthopaedics, Oct. 1999, pp. 309-317, vol. 9, No. 4.
Nakano et al., "Interference screw fixation of double flexor tendon graft in anterior cruciate ligament reconstruction—biomechanical evaluation with cyclic elongation," Clinical Biomechanics, 2000, pp. 188-195, vol. 15.
Petrie et al., "Double Bundle Posterior Cruciate Ligament Reconstruction Technique: University of Pittsburgh Approach," Operative Techniques in Sports Medicine, Jul. 1999, pp. 118-126, vol. 7, No. 3.
Trout et al., "Rupture of the Tibialis Anterior Tendon," The Journal of Foot & Ankle Surgery, 2000, pp. 54-58, vol. 39, No. 1.
Veltri et al., "Treatment of Acute and Chronic Injuries to the Posterolateral and Lateral Knee," Operative Techniques in Sports Medicine, Jul. 1996, pp. 174-181, vol. 4, No. 3.
Yamanaka et al., "The Effect of Cyclic Displacement on the Biomechanical Characteristics of Anterior Cruciate Ligament Reconstructions," American Journal of Sports Medicine, Jun. 1999, pp. 772-777, vol. 27, No. 6.
Arthrex, Inc., "Speed and Precision in Knotless Rotator Cuff Repair," at least as early as Apr. 18, 2010.
Trenhaile, "Biceptor Tenodesis System Offers All-Inside Option to Biceps Tendon Repair," Joint Intelligence, at least as early as Apr. 18, 2010, pp. 1-7, vol. 1, Issue 1, Smith & Nephew.
Brand, Jr., et al., "Graft Fixation Issues in Knee Ligament Surgery," Operative Techniques in Orthopaedics, Oct. 1999, pp. 256-263, vol. 9, No. 4.
Dalton, Jr., et al., "Surgical Techniques to Correct Nonanatomic Femoral Tunnels," Operative Techniques in Sports Medicine, Apr. 1998, pp. 83-90, vol. 6, No. 2.
Fithian et al., "Fixation in Knee Ligament Repair and Reconstruction," Operative Techniques in Orthopaedics, Apr. 1992, pp. 63-70, vol. 2, No. 2.
Hara et al., "A New Arthroscopic Method for Reconstructing the Anterior and Posterior Cruciate Ligaments Using a Single-Incision Technique: Simultaneous Grafting of the Autogenous Semitendinosus and Patellar Tendons," Arthroscopy: The Journal of Arthroscopic and Related Surgery, Nov./Dec. 1999, pp. 871-876, vol. 15, No. 8.
Matthews et al., "Fixation Strengths of Patellar Tendon-Bone Grafts," Arthroscopy: The Journal of Arthroscopic and Related Surgery, Feb. 1993, pp. 76-81, vol. 9, No. 1.
To et al., "Contributions of Femoral Fixation Methods to the Stiffness of Anterior Cruciate Ligament Replacements at Implantation," Arthroscopy: The Journal of Arthroscopic and Related Surgery, May/Jun. 1999, pp. 379-387, vol. 15, No. 4.

\* cited by examiner

TENODESIS FIXATION METHOD

CROSS-REFERENCE TO RELATED APPLICATIONS

This application claims the benefit of Australian Provisional Patent Application No. 2009901634, filed Apr. 17, 2009, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND

1. The Field of the Present Disclosure

The present disclosure relates generally to medical devices and methods, and more particularly, but not necessarily entirely, to medical devices and methods for fixating tissues or implants to bones.

2. Description of Related Art

Tenodesis is a fixation of an end of a tendon to a bone. Tenodesis may be necessary for the treatment of tendonopathy or tears in a tendon. Bicep tenodesis may be necessary to treat biceps instability typically in association with a rotator cuff tear. Open surgical techniques have been developed to perform tenodesis procedures. Open surgical techniques, however, are becoming more disfavored due to increased recovery times and patient trauma. More recently, minimally invasive techniques for tenodesis procedures have been developed to reduce soft tissue trauma and recovery time. For example, arthroscopic techniques have been developed using interference fit screw fixation. These techniques may involve drilling a bore into a bone and then anchoring the tendon to the bone using a threaded screw. One drawback to these previous techniques is that the tendon may not be properly placed in the bore of the bone.

The prior art is thus characterized by several disadvantages that are addressed by the present disclosure. The present disclosure minimizes, and in some aspects eliminates, the above-mentioned failures, and other problems, by utilizing the methods and structural features described herein. The features and advantages of the present disclosure will be set forth in the description which follows, and in part will be apparent from the description, or may be learned by the practice of the present disclosure without undue experimentation. The features and advantages of the present disclosure may be realized and obtained by means of the instruments and combinations particularly pointed out in the appended claims.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
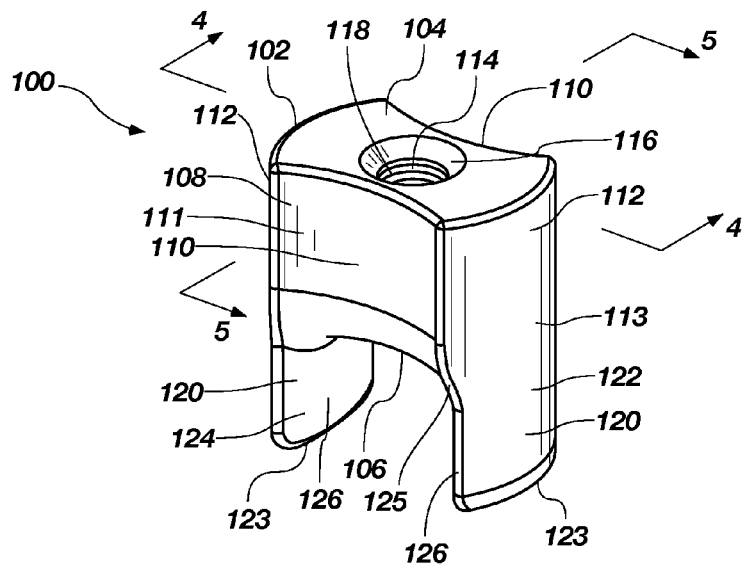
FIG. 1 is a perspective view of an implant pursuant to an embodiment of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise. In describing and claiming the present disclosure, the following terminology will be used in accordance with the definitions set out below. As used herein, the terms "comprising," "including," "containing," "characterized by," and grammatical equivalents thereof are inclusive or open-ended terms that do not exclude additional, unrecited elements or method steps. As used herein, the term "implant" refers to a thing that remains inside of a body of a patient.

Applicants have discovered a novel anchoring device for securing tissue, such as a tendon, to a bone. The anchoring device may comprise a first stage and a second stage, which may be non-integral with each other. The first stage may include an implant and the second stage may include a fixation member for securing the tissue to the bone. The implant may removably engage an end of a push rod. Using the push rod, a surgeon may be able to guide a portion of the tissue into a pre-drilled bore in the bone with the implant. The tissue may be pushed or pinned against a bottom surface of the bore by applying a force to the end of the push rod outside of the body. The fixation member may be installed in the bore of the bone while maintaining sufficient force on the push rod. The fixation member may slide over the push rod to engage the bore. In this manner, the tissue may be firmly pinned against the bottom surface of the bore while the fixation member is installed. Once the fixation member has been installed, the push rod may be disengaged from the implant. The implant may remain in the bore permanently after the surgery.

Referring now to FIGS. 1-5, there is depicted an implant 100 pursuant to an embodiment of the present disclosure. The implant 100 may comprise a body member 102. The body member 102 may include a substantially planar top surface 104 and a bottom surface 106. The body member 102 may further comprise a sidewall 108 extending from the top surface 104 to the bottom surface 106. The sidewall 108 may comprise a pair of relief channels 110 disposed on opposite sides of the body member 102. Each of the relief channels 110 may include a concave surface 111. The relief channels 110 may extend longitudinally from the top surface 104 to the bottom surface 106 of the body member 102. As will be explained in more detail herein after, the relief channels 110 may allow passage of a tendon between the body member 102 and a sidewall of a bore in a bone. The relief channels 110 may further lead into a straddle formed underneath the body member 102.

The sidewall 108 of the body member 102 may further comprise a pair of side portions 112. The side portions 112 may include a convex surface 113. Each of the side portions 112 may be disposed on opposing sides of the body member 102. Each of the side portions 112 may extend laterally between the relief channels 110.

The top surface 104 may have a bore 114 that extends into the body member 102. A tapered portion 116 may be interposed between the top surface 104 and the bore 114. The bore 114 may include a threaded inner sidewall 118. As will be explained in more detail herein after, the threaded inner sidewall 118 may engage a threaded end of a push rod.

In an embodiment of the present disclosure, the implant 100 may be non-slidably engaged to the end of a push rod. For example, the implant 100 may not be able to slid along the push rod once it is installed. In an embodiment of the present disclosure, a push rod may not extend through or beyond the body member 102 of the implant 100. The implant 100 may further comprise a pair of legs 120. The legs 120 may extend downwardly from the body member 102. The legs 120 may extend below the bottom surface 106 of the body member 102. Each of the legs 120 may terminate at a free end 123. Each of the legs 120 may include an outer sidewall 122. The outer sidewalls 122 of the legs 120 may be contiguous with the side portions 112 of the sidewall 108 of the body member 102. The outer sidewalls 122 of the legs 120 may be convex. Each of the legs 120 may further include an inner sidewall 124. The inner sidewalls 124 of the legs 120 may be facing each other. The inner sidewalls 124 of the legs 120 may join the bottom surface 106 of the body member 102. A taper 125 may be disposed between the body member 102 and each of the legs 120.

The legs 120 may define the lateral limits of a straddle 126. The bottom surface 106 of the body member 102 may define the uppermost limit of the straddle 126. The free ends 123 of the legs 120 may define the lowermost limit of the straddle 126. The lowermost limit of the straddle 126 may be open. As will be explained in more detail hereinafter, the straddle 126 may be installed onto a portion of a tendon without the need of threading a tendon through an eyelet. The implant 100 may be characterized by the absence of any bone engaging structures.

Figure 2:
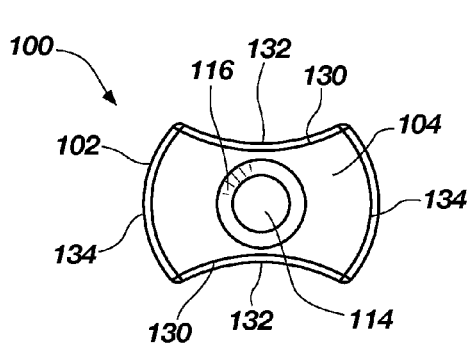
FIG. 2 is a top view of the implant depicted in FIG. 1.
Figure 4:
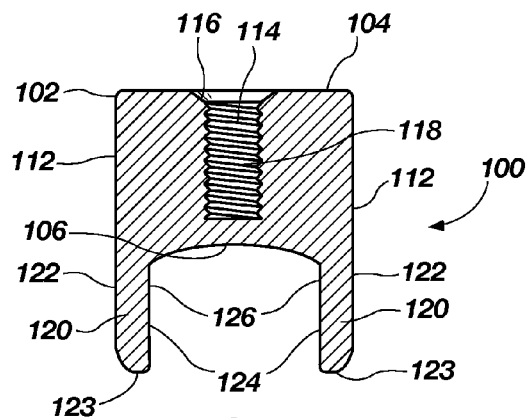
FIG. 4 is a cross-sectional view of the implant depicted in FIG. 1 taken along the section 4-4.
Figure 3:
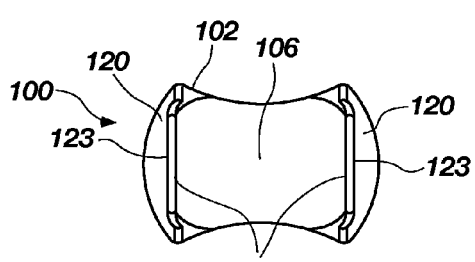
FIG. 3 is a bottom view of the implant depicted in FIG. 1.
Figure 5:
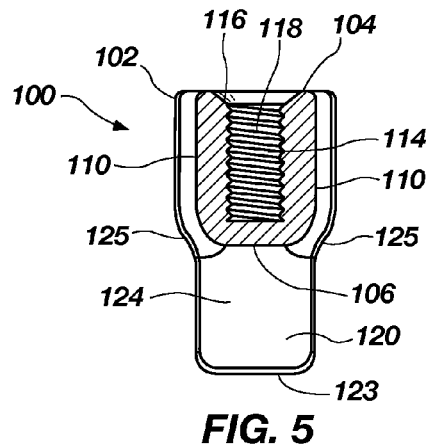
FIG. 5 is a cross-sectional view of the implant depicted in FIG. 1 taken along the section 5-5.

As perhaps best seen in FIG. 2, the top surface 104 of the body member 102 may include a pair of concave edges 130 disposed on opposing sides of the top surface 104. The concave edges 130 may form a waist 132 in the top surface 104. The bore 114 may align with the waist 132. The body member 102 may include a pair of convex edges 134 disposed on opposing sides of the top surface 104. Each of the convex edges 134 may extend between the concave edges 130, but on opposite sides of the top surface 104. The top surface 104 may be approximately shaped as an hourglass.

Figure 6:
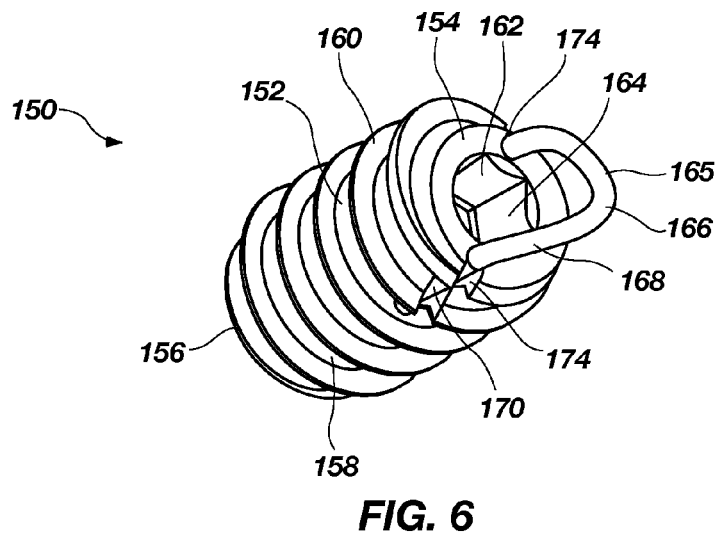
FIG. 6 is a perspective view of a fixation member pursuant to an embodiment of the present disclosure.
Figures 7, 8:
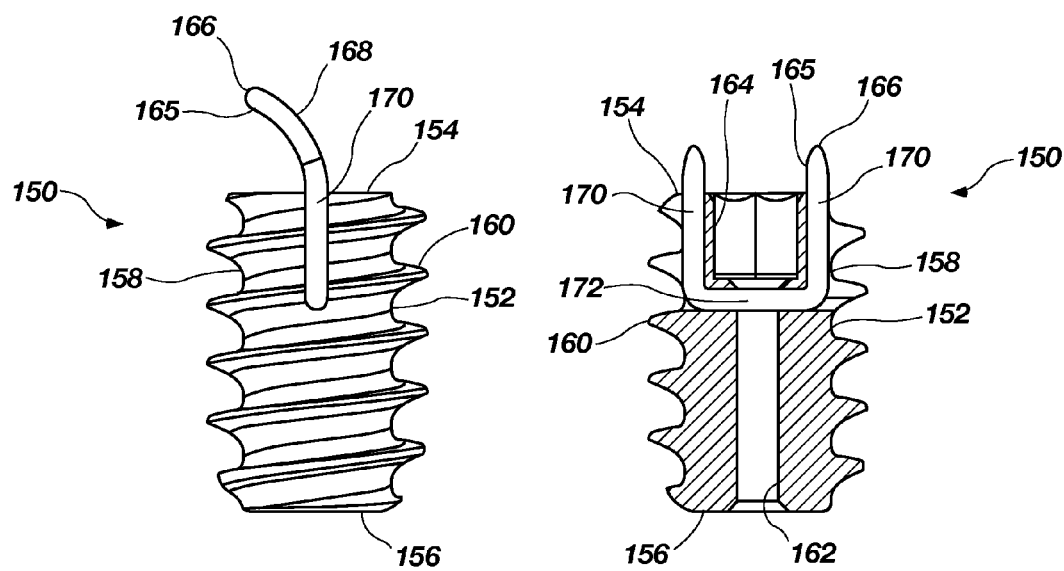
FIG. 7 is a side view of the fixation member depicted in FIG. 6.
FIG. 8 is a cross-sectional view of the implant depicted in FIG. 6.

Referring now to FIGS. 6-8, there is shown a fixation member 150 pursuant to an embodiment of the present disclosure. As will be explained in more detail hereinafter, the fixation member 150 may be operable to secure a tendon to a bone. The fixation member 150 may also secure an implant into a pre-drilled bore in a bone. The fixation member 150 may include a cylindrical and elongate body 152. The body 152 of the fixation member 150 may extend from a proximal end 154 to a distal end 156. An outer surface 158 of the body 152 of the fixation member 150 may include threads 160 for engaging a sidewall of a bore in a bone.

A throughbore 162 may extend in the from the proximal end 154 to the distal end 156 of the body 152 of the fixation member 150. As will be explained in more detail hereinafter, the throughbore 162 may be dimensioned to allow passage of a push rod. As will be explained in more detail hereinafter, a topmost portion 164 of the throughbore 162 may be configured for engaging a tip of a drive shaft. In an embodiment of the present disclosure, the topmost portion 164 may comprise a socket, which may be a hex socket or a TORX™ socket.

The fixation member 150 may include a suture anchor 165. The suture anchor 165 may include a loop 166 may extend above the proximal end 154 of the fixation member 150. The loop 166 may include a curvature 168 such that it does not interfere with the insertion of a drive shaft into the topmost portion 164 of the throughbore 162. The loop 166 may connect to a pair of opposing side members 170. The opposing side members 170 may be connected by a cross-piece member 172. The body 152 of the fixation member 150 may include a pair of slots 174 disposed on opposing sides of the body 152. The slots 174 may extend from the proximal end 154 towards the distal end 156 of the fixation member 150. The slots 174 may pass through, and bisect the threads 160. The opposing side members 170 may be disposed in the slots 174. The slots 174 may have sufficient depth such that the side members 170 do not interfere with threads 160. The cross-piece member 172 may extend laterally through the body 152. The cross-piece member 172 may not interfere with the throughbore 162. It will be appreciated that the suture anchor 165 is optional, such that the fixation member 150 may include the suture anchor 165, or the fixation member 150 may alternatively be constructed without the suture anchor 165.

Referring now to FIGS. 9-13, there is depicted a surgical method of tenodesis that may include anchoring a tendon 200 to a bone 202 pursuant to an embodiment of the present disclosure. In an embodiment of the present disclosure, the tendon 200 may be a biceps tendon and the bone 202 may be a humerus bone. It will be appreciated the present disclosure may be adapted for use with other tendons and bones in a human body, or a body of any living animal. In will further be appreciated that the present disclosure may be adapted for use with other body tissues and implants. The surgical method shown in FIGS. 9-13 may be utilized using open surgical techniques or minimally invasive surgical techniques such as arthroscopic surgical techniques.

Figure 9:
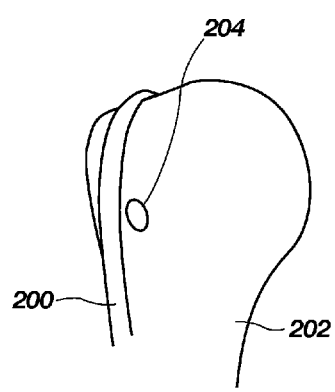
FIG. 9 is a perspective view of a head of a bone having been pre-drilled with a bore for a tenodesis procedure.

Starting with FIG. 9, a bore 204 may be formed in the bone 202 by a surgeon. In an embodiment of the present disclosure, the bore 204 may be formed using a bone drill, a micro-bone drill, a punch, or any other suitable device for forming the bore 204 in the bone 202 as is known to one having ordinary skill in the art. The bore 204 may have a depth and diameter. The depth and diameter of the bore 204 may be dependent on several factors, including the relative size of the tendon 200 and the bone 202. In an embodiment of the present disclosure, the depth of the bore 204 may be about 25 millimeters and the diameter may be about 8 millimeters. In an embodiment of the present disclosure, the depth of the bore 204 may be between about 18 millimeters and 32 millimeters. In an embodiment of the present disclosure, the diameter of the bore 204 may be between about 5 millimeters and 12 millimeters. The tendon 200 may or may not need to be displaced in order to form the bore 204 in the bone 202.

In an embodiment of the present disclosure, an end (not explicitly shown) of the tendon 200 may be still attached to its original anchor point. For example, if the tendon 200 is a biceps tendon, then the end of the tendon 200 may be attached to its normal attachment point on the shoulder (not shown). In an embodiment of the present disclosure, the tendon 200 may have suffered trauma severing it from its original attachment point on the shoulder (not shown). In an embodiment of the present disclosure, the tendon 200 may have been subject to a previous tenodesis procedure that has failed.

Figure 10:
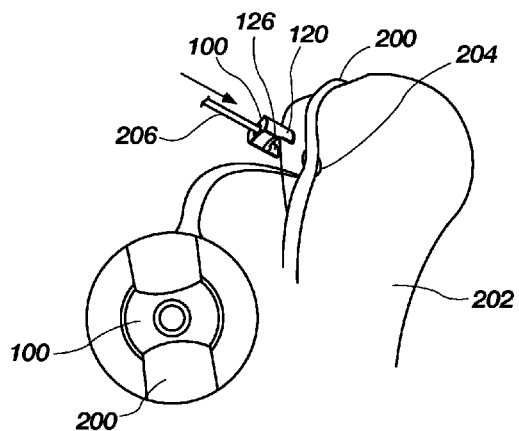
FIG. 10 is a perspective view of the head of the bone depicted in FIG. 9 further showing an insertion of a tendon into the pre-drilled bore using an implant affixed to an end of a push rod.

Referring now to FIG. 10, the implant 100 may be removably attached to an end of a push rod 206. In an embodiment of the present disclosure, the push rod 206 may be a K-wire. The push rod 206 may include a threaded terminal end for engaging the threaded bore 114 in the body member 102 of the implant 100. In an embodiment of the present disclosure, the implant 100 may include a socket for receiving an end of a push rod that has been designed to fit in the socket. In an embodiment of the present disclosure, the implant 100 may include a threaded male shaft extending from the body member 102 that engages a threaded female bore on an end of a push rod.

Figure 11:
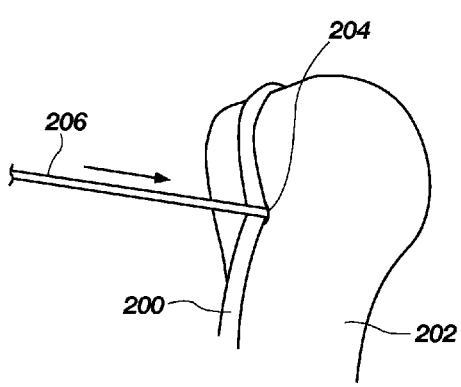
FIG. 11 is a perspective view of the head of the bone depicted in FIG. 9 further showing the implant pushing the tendon into the pre-drilled bore.

Using the push rod 206, a surgeon may guide the implant 100 such that the tendon 200 is disposed in the straddle 126. In particular, the legs 120 may straddle the tendon 200. Once the tendon 200 has been placed in the straddle 126, the surgeon may then apply a force to the push rod 206 to thereby push or install the implant 100 into the bore 204. The portion of the tendon 200 confined in the straddle 126 may also be pushed into the bore 204 such that the tendon 200 runs into and out of the bore 204 as shown in FIG. 11. The surgeon may apply a force to the push rod 206 to thereby push the tendon 200 to a desired depth in the bore 204. In an embodiment of the present disclosure the surgeon may apply sufficient force to the push rod 206 such that the tendon 200 abuts with, or is pinned against, a bottom surface of the bore 204. In an embodiment of the present disclosure, the surgeon may apply sufficient force such that the free ends 123 of the legs 120 abut against the bottom surface of the bore 204. In an embodiment of the present disclosure, the surgeon may apply sufficient force such that the free ends 123 of the legs 120 are driven into a bottom surface of the bore 204. In an embodiment of the present disclosure, the free ends 123 of the legs 120 may be contoured to conform to a contoured bottom of the bore 204. The free ends 123 of the legs 120 may be have sufficient width such that the free ends 123 engage a bottom surface of the bore 204 with a line contact and not a point contact.

Figure 12:
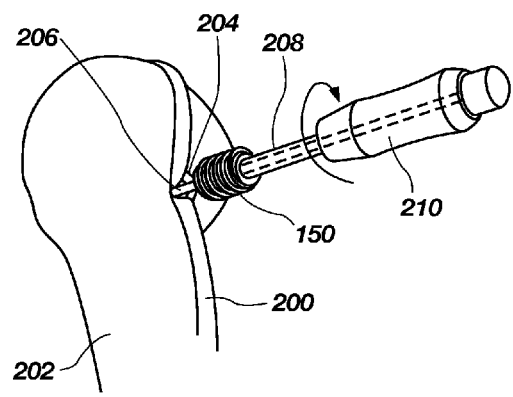
FIG. 12 is a perspective view of the head of the bone depicted in FIG. 9 further showing an installation of a fixation member using a drive tool.

As show in FIG. 12, with the surgeon continuing to apply a force to the push rod 206 to thereby maintain the tendon 200 at a desired depth in the bore 204, the fixation member 150 may be installed into the bore 204 in a manner that will now be explained. The fixation member 150 may be installed onto an end of a drive shaft 208. For example, the end of the drive shaft 208 may be configured to engage a socket in the topmost portion 164 of the throughbore 162 of the fixation member 150.

In an embodiment of the present disclosure, the drive shaft 208 may include a hollow passageway 210 dimensioned for allowing passage of the push rod 206. The push rod 206 may extend through the throughbore 162 of the fixation member 150 and the hollow passageway 210 in the drive shaft 208. The position of the push rod 206 with respect to the drive shaft 208 may be variable. In an embodiment of the present disclosure, the push rod 206 may extend into and out of the hollow passageway 210 of the drive shaft 208. The push rod 206 may telescopically engage the drive shaft 208.

As mentioned, with the surgeon maintaining a force on the push rod 206 to thereby push the tendon 200 to a desired depth in the bore 204, the fixation member 150 may be slid down the push rod 206 until its lowermost thread contacts an opening to the bore 204. At this point, with the surgeon still maintaining a force on the push rod 206, the fixation member 150 may be rotated using the drive shaft 208 such that the fixation member 150 engages a sidewall of the bore 204. The fixation member 150 is advanced in the bore 204 to the desired depth. It will be appreciated that neither the push rod 206 nor the implant 100 may rotate during this procedure.

Figure 13:
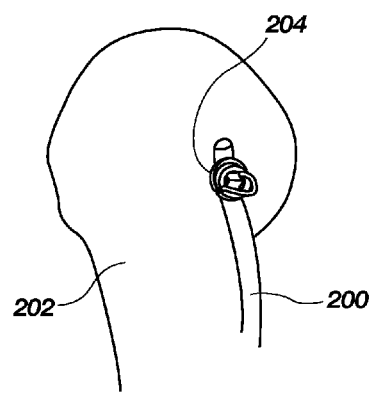
FIG. 13 is a perspective view of the head of the bone depicted in FIG. 9 further showing the fixation member installed into the bore over the implant.

As shown in FIG. 13, once the fixation member 150 has reached the desired depth, the push rod 206 and the drive shaft 208 may be removed. In regard to the push rod 206, this may require disengaging the end of the push rod 206 from the implant 100. In an embodiment of the present disclosure, this may be accomplished by rotating the push rod 206 such that the threads on the end of the push rod 206 disengage the threaded bore 114 of the implant 100. In regard to the drive shaft 208, this may be accomplished by simply withdrawing the end of the drive shaft 208 out of the socket formed in the topmost portion 164 of the throughbore 162.

It will be appreciated that because the dimensions of the implant 100 are greater than that of the throughbore 162 in the fixation member 150, that the implant 100 is permanently installed into the bore 204 until the fixation member 150 is removed, which may be never. Thus, the implant 100 remains permanently inside of the bone 202 of the patient after the surgery. Further, the side of the tendon 200 opposite the muscle and extending from the bore 204 may be trimmed by the surgeon as shown in FIG. 13.

Figure 14:
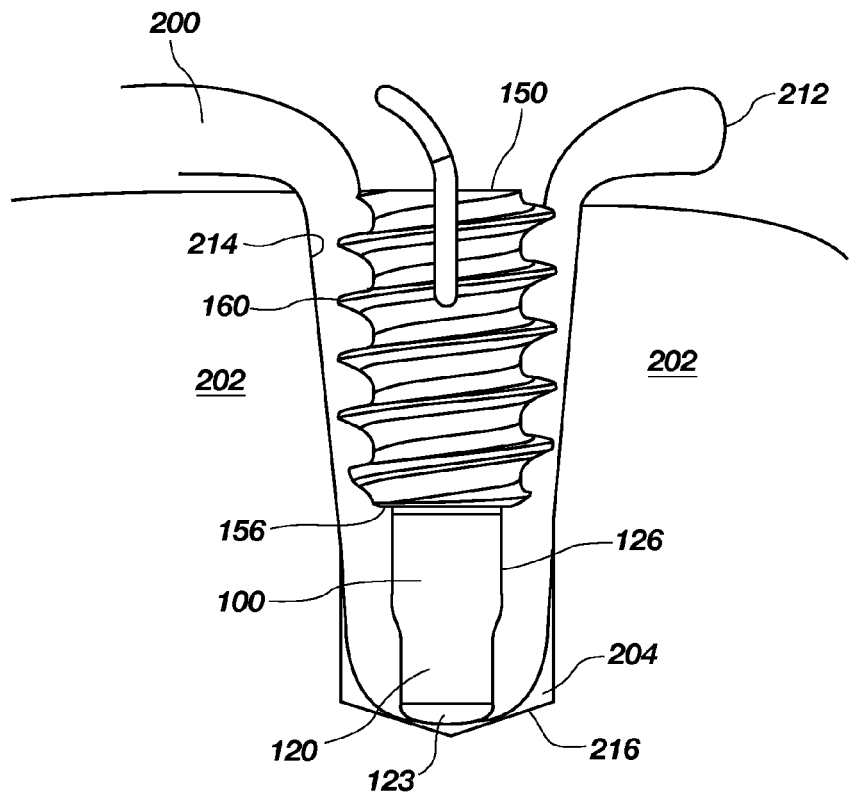
FIG. 14 depicts a tendon affixed in a bore in a bone by an implant and a fixation member.

Referring now to FIG. 14, there is shown a view of the implant 100 and fixation member 150 installed in the bore 204. The tendon 200 may extend into the bore 204 between the fixation member 150 and a sidewall 214 of the bore 204. The tendon 200 may then pass through the straddle 126, between the fixation member 150 and the sidewall 214, and then exit the bore 204. The tendon 200 may then terminate at a trimmed end 212. It will be appreciated that the tendon 200 forms a half-loop, or U-shaped structure, inside of the bore 204 and around the straddle 126.

The threads 160 of the fixation member 150 may engage and compress the tendon 200 against the sidewall 214 of the bore 204. The engagement of the tendon 200 between the fixation member 150 and sidewall 214 may securely anchor the tendon 200 to the bone 202. The threads 160 of the fixation member 150 may further engage the sidewall 214 of the bore 204 to the secure the fixation member 150 to the bone 202.

The advancement of the fixation member 150 into the bore 204 may drive the free ends 123 of the legs 120 of the implant 100 into an engagement with a bottom surface 216 of the bore 204. Further, the advancement of the fixation member 150 may pin or compress the tendon 200 between the implant 100 and the bottom surface 216 of the bore 204. In particular, the distal end 156 of the fixation member 150 may abut against, and apply a force to, the top surface 104 of the implant 100 as the fixation member 150 is advanced into the bore 204. The top surface 104 may be dimensioned larger than the diameter of the throughbore 162 of the fixation member 150.

It will be appreciated that the ability to apply a force to the push rod 206 while installing the fixation member 150 may ensure that the tendon 200 is seated to the proper depth in the bore 204 when the fixation member 150 is installed. Further, the use of the implant 100 may ensure that the tendon 200 cannot slide up the shaft of the push rod 206 during installation of the fixation member 150. Further, because the push rod 206 may disengage the implant 100, the implant 100 may remain in the bore 204 such that the tendon 200 remains confined by the straddle 126 of the implant 100.

It will be further appreciated that the relief channels 110 formed in the sidewall 108 of the body member 102 (see FIG. 1) of the implant 100 may allow clearance between the implant 100 and the sidewall 214 of the bore 204. The relief channels 110 may ensure that the tendon 200 does not prevent the implant 100 from being inserted to a desired depth in the bore 204. For example, a thickness of the tendon 200 may prevent the implant 100 from being installed into the bore 204 if not for the presence of the relief channels 110. It will be appreciated that the relief channels 110 are optional, such that the implant 100 may be constructed to include the relief channels 110, and the implant 100 may alternatively be constructed without any relief channels 110.

Figure 15:
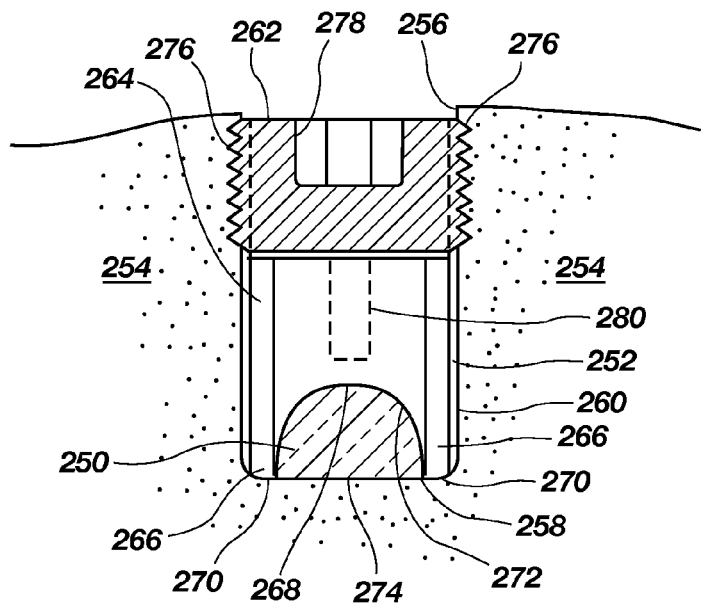
FIG. 15 depicts a tendon affixed in a bore in a bone by an implant and a fixation member.

Referring now to FIG. 15, there is depicted a cross-sectional view of a tendon 250 fixated in a bore 252 in a bone 254 pursuant to an embodiment of the present disclosure. The bore 252 may comprise an opening 256 and a bottom surface 258. A bore sidewall 260 may extend from the opening 256 to the bottom surface 258.

An implant 264 may be implanted into the bore 260. The implant 264 may have a bottom surface 268 and a pair of spaced apart legs 266. Each of the legs 266 may extend downwardly from the bottom surface 268 and terminate at a free end 270. The free ends 270 of the legs 266 may abut against the bottom surface 258 of the bore 252. The legs 266 and the bottom surface 268 of the implant 264 may define a saddle or straddle 272. The saddle 272 is mounted on the tendon 250 such that the legs 266 straddle the tendon 250. A surface 274 of the tendon 250 is in contact with the bottom surface 258 of the bore 252.

A fixation member 262 may be installed above the implant 264 in the bore 252. The fixation member 262 may comprise bone engagement structure 276 operable to engage the sidewall 260 of the bore 252 and hold the fixation member 262 in place. In an embodiment of the present disclosure, the bone engagement structure 276 may comprise threads. In an embodiment of the present disclosure, the bone engagement structure 276 may comprise barbs.

The fixation member 262 may comprise a mating member 278 for engaging a drive shaft or push rod (not shown). In an embodiment of the present disclosure, the mating member 278 may comprise a socket or a bore. In an embodiment of the present disclosure, the mating member 278 may comprise threads. In an embodiment of the threaded disclosure, the mating member 278 may comprise a threaded or unthreaded inner sidewall of a bore. In an embodiment of the present disclosure, the mating member 278 may comprise a threaded or an unthreaded shaft.

The implant 264 may comprise a mating member 280 for engaging a drive shaft or push rod (not shown). In an embodiment of the present disclosure, the mating member 280 may comprise a socket or a bore. In an embodiment of the present disclosure, the mating member 280 may comprise threads. In an embodiment of the threaded disclosure, the mating member 280 may comprise a threaded or unthreaded inner sidewall of a bore. In an embodiment of the present disclosure, the mating member 280 may comprise a threaded or an unthreaded shaft.

Figure 16:
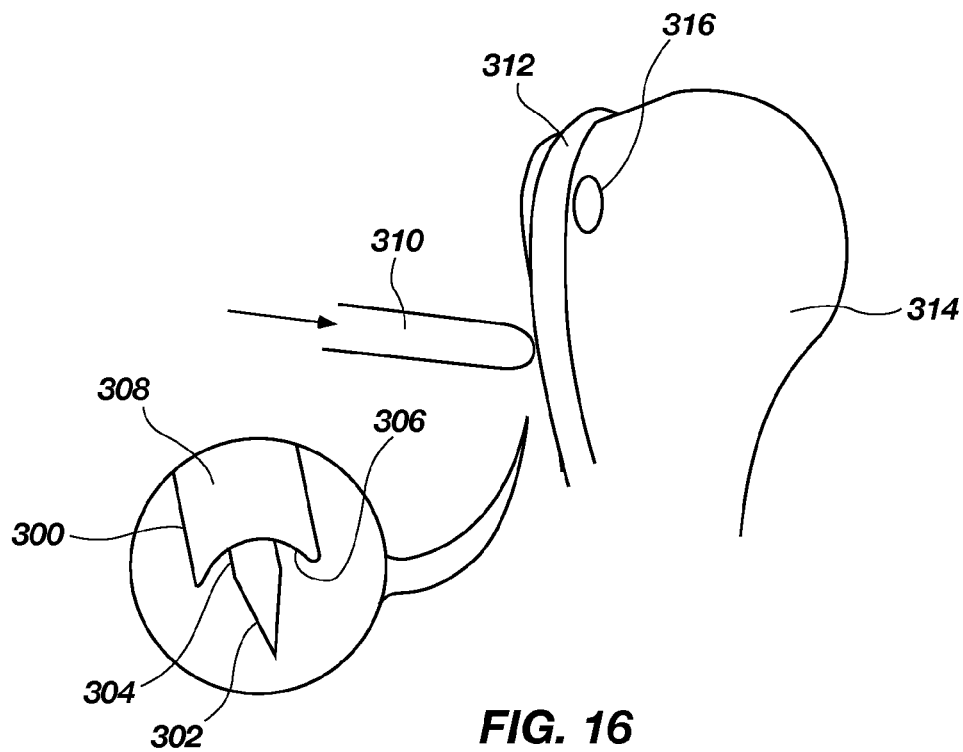
FIG. 16 is a perspective view of a head of a bone and a tool for pinning a tendon to the bone.
Figure 17:
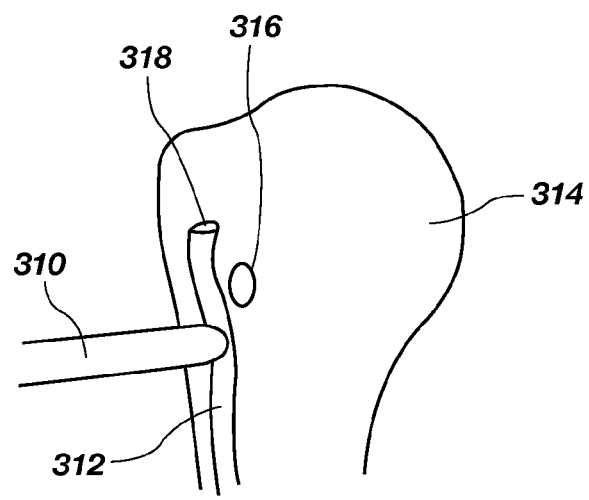
FIG. 17 is a perspective view of a head of a bone and a tool for pinning a tendon to the bone.

Referring now to FIGS. 16 and 17, there is depicted a surgical device 300 suitable for use in a tenodesis surgical procedure. In an embodiment of the present disclosure, the surgical device 300 may be suitable for use with arthroscopic tenodesis techniques. The device 300 may include a point or tip 302 formed on the end of a shaft 304. The device 300 may further include a straddle 306 formed on the end of an elongate member 308. The device 300 may include a handle (not shown).

In use, the device 300 is inserted through an arthroscopic cannula 310 and is brought to bear against a tendon 312. Sufficient force is applied to the device 300 to anchor the tendon 312 against a bone 314 using the point 302. In an embodiment of the present disclosure, the point 302 may penetrate through the tendon 312 and into the bone 314. The straddle 306 may assist in holding and trapping the tendon 312 against the bone 314. Once pinned in place, the tendon 312 may be trimmed or cut as shown in FIG. 17. As shown in FIGS. 16 and 17, a bore 316 may be pre-drilled below the anticipated end of the tendon 312 such that cutting of the tendon 312 does not cause retraction of the tendon 312 past the bore 316. With the bore 316 positioned between a free end 318 of the tendon 312 and the pinning location by the device 300, the tendon 312 may be anchored to the bone 314 in the bore 316 using an implant and fixation device as disclosed herein.

Referring now to FIGS. 22-26, there is depicted an embodiment of a fixation member 350 pursuant to an embodiment of the present disclosure. The fixation member 350 may be operable to secure a tendon to a bone. The fixation member 350 may also secure an implant into a pre-drilled bore in a bone. The fixation member 350 may include a cylindrical and elongate body 352. The body 352 of the fixation member 350 may extend from a proximal end 354 to a distal end 356. An outer surface 358 of the body 352 of the fixation member 350 may include threads 360 for engaging a sidewall of a bore in a bone.

A throughbore 362 may extend in the from the proximal end 354 to the distal end 356 of the body 352 of the fixation member 350. The throughbore 362 may be dimensioned to allow passage of a push rod. A topmost portion 364 of the throughbore 362 may be configured for engaging a tip of a drive shaft. The topmost portion 364 may comprise a mating member, such as a socket. The socket may be a hex socket or a TORX™ socket. A top thread 366 of the threads 360 may stop short of the proximal end 354 of the body 352 to thereby form a relief channel 368. A second thread 370 of the threads 360 may also include a relief channel 372. The relief channels 368 and 372 may ensure that the threads 360 do not sever a tendon fixated by the fixation member 350.

Referring now to FIGS. 27-32, there is depicted an implant 400 pursuant to an embodiment of the present disclosure. The implant 400 may comprise a body member 402. The body member 402 may include a substantially planar top surface 404 and a bottom surface 406. The body member 402 may further comprise a sidewall 408 extending from the top surface 404 to the bottom surface 406. The sidewall 408 may comprise a pair of relief channels 410 disposed on opposite sides of the body member 402. Each of the relief channels 410 may include a concave surface. The relief channels 410 may extend longitudinally from the top surface 404 to the bottom surface 406 of the body member 402. The relief channels 410 may allow passage of a tendon between the body member 402 and a sidewall of a bore in a bone. The relief channels 410 may further lead into a straddle 426 formed underneath the body member 402.

The sidewall 408 of the body member 402 may further comprise a pair of side portions 412. Each of the side portions 412 may be disposed on opposing sides of the body member 402. Each of the side portions 412 may extend laterally between the relief channels 410. The top surface 404 may have a bore 414 that extends into the body member 402. A tapered portion 416 may be interposed between the top surface 404 and the bore 414. The bore 414 may include a threaded inner sidewall 418. The threaded inner sidewall 418 may engage a threaded end of a push rod.

The implant 400 may further comprise a pair of legs 420. The legs 420 may extend downwardly from the body member 402. The legs 420 may extend below the bottom surface 406 of the body member 420. Each of the legs 420 may terminate at a free end 423. Each of the legs 420 may include an outer sidewall 422. Each of the legs 420 may further include an inner sidewall 424. The inner sidewalls 424 of the legs 420 may be facing each other. The inner sidewalls 424 of the legs 420 may join the bottom surface 406 of the body member 402.

The legs 420 may define the lateral limits of the straddle 426. The bottom surface 406 of the body member 402 may define the uppermost limit of the straddle 426. The free ends 423 of the legs 420 may define the lowermost limit of the straddle 426. The lowermost limit of the straddle 126 may be open such that the straddle 426 may be installed onto a portion of a tendon without the need of threading the tendon into an eyelet.

Figure 28:
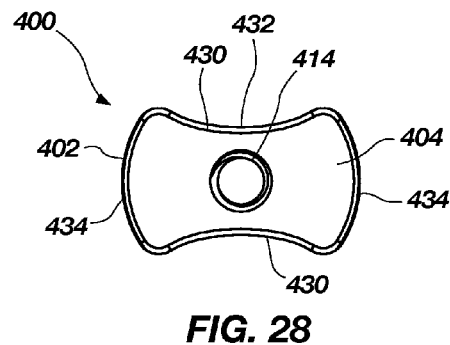
FIG. 28 is a top view of the implant depicted in FIG. 27.
Figure 29:
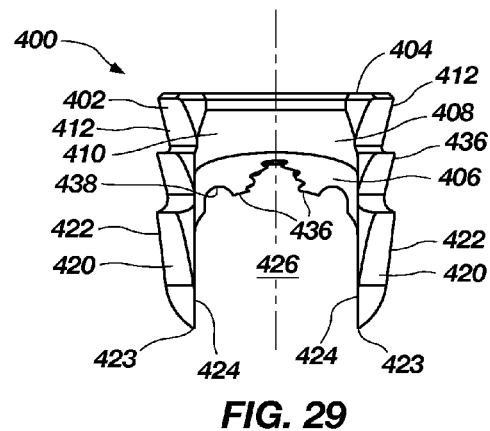
FIG. 29 is a side view of the implant depicted in FIG. 27.
Figure 30:
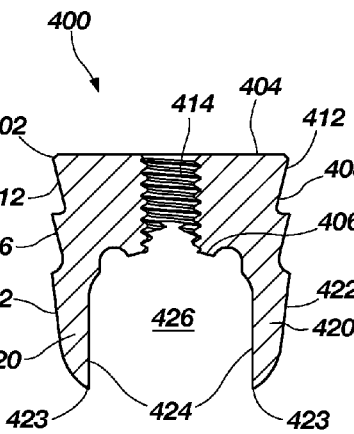
FIG. 30 is a side view of the implant depicted in FIG. 27.
Figure 31:
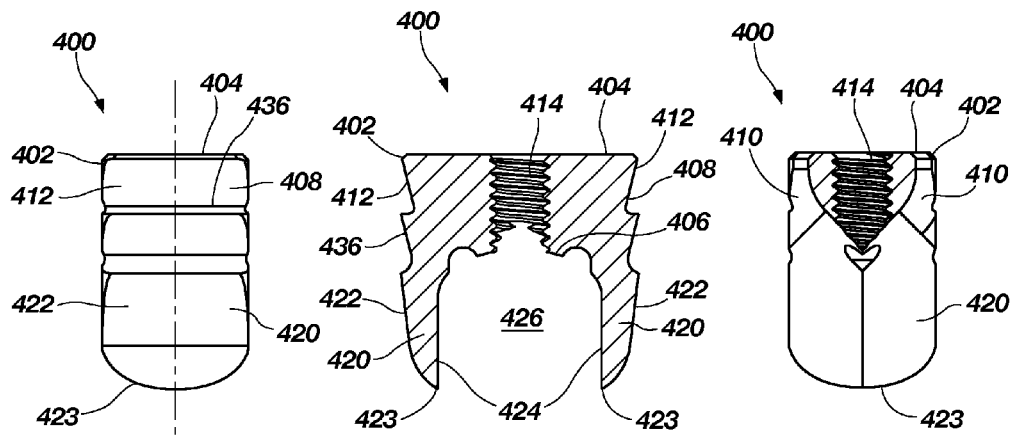
FIG. 31 is a cross-sectional view of the implant depicted in FIG. 27.
Figure 32:
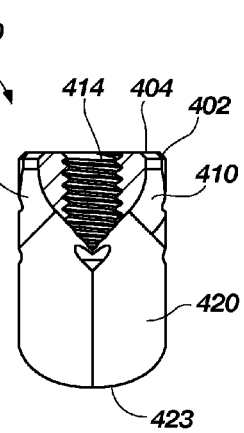
FIG. 32 is a cross-sectional view of the implant depicted in FIG. 27.

As perhaps best seen in FIG. 28, the top surface 404 of the body member 402 may include a pair of concave edges 430 disposed on opposing sides of the top surface 404. The concave edges 430 may form a waist 432 in the top surface 404. The bore 414 may align with the waist 432. The body member 402 may include a pair of convex edges 434 disposed on opposing sides of the top surface 404. Each of the convex edges 434 may extend between the concave edges 430, but on opposite sides of the top surface 404. The top surface 404 may be approximately shaped as an hourglass.

A plurality of bone engaging structures 436 may extend from the implant 400. The bone engaging structures 436 may be configured and adapted for engaging an inner sidewall of a bore in a bone. In an embodiment of the present disclosure, the bone engaging structures 436 may comprise barbs. Bone engaging structures may extend from the outer side wall 422 of the legs 420. It will be appreciated that the bone engaging structures 436 may be optional, such that the implant 400 may be constructed to include bone engaging structures 436, and the implant 400 may alternatively be constructed without any bone engaging structures 436.

The bottom surface 406 of the body member 402 may comprise tendon engagement members 436. The tendon engagement members 436 may be relatively jagged, sharp or pointed for engaging or even penetrating a surface of a tendon. The tendon engagement members 436 may be operable to hold a tendon immovable relative to the implant 400. In an embodiment of the present disclosure, the tendon engagement members 436 comprise a plurality of teeth. In an embodiment of the present disclosure, the tendon engagement members 436 may comprise spikes. The tendon engagement members 436 may also be referred to herein as engagement members 436.

In an embodiment of the present disclosure, semi-circular gaps 438 may be disposed amongst the engagement members 436. It will be appreciated that the engagement members 436 may be integrally formed in the implant 400 such that they remain in a bore in a bone after surgery.

Figure 33:
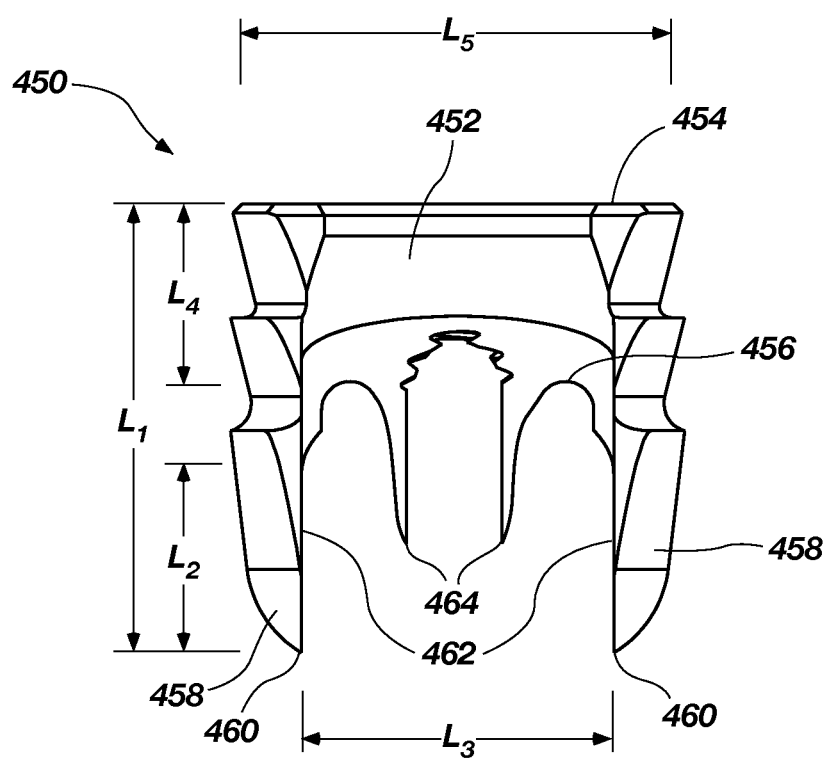
FIG. 33 is a side view of an implant according to an embodiment of the present disclosure.

Referring now to FIG. 33, there is depicted an implant 450 pursuant to an embodiment of the present disclosure. The implant 450 may comprise a body member 452 having a top surface 454 and a bottom surface 456. The implant 450 may further comprise a pair of legs 458 extending downwardly from the body member 452. Each of the legs 458 may terminate at a free end 460. The legs 458 may define a straddle 462. Extending downwardly from the bottom surface 456 of the body member 452 may be tendon engagement structures 464. The tendon engagement structures 464 may hold a tendon immobile with respect to the implant 450. In an embodiment of the present disclosure, the tendon engagement structures 464 may comprise at least one spike which may penetrate into a tendon.

In an embodiment of the present disclosure, the tendon engagement structures 464 may comprise at least one spike comprising a pair of spaced apart spikes 464 extending parallel to, and between the pair of legs 458, wherein a distance between the pair of legs 458 is $L_3$, wherein a lateral distance between a first leg 458 and a first spike 464 is about 0.33 of $L_3$, wherein a lateral distance between the first spike 464 and the second spike 464 is about 0.33 of $L_3$, and wherein a lateral distance between the second spike 464 and a second leg 458 is about 0.33 of $L_3$. It is to be understood that the ratio "0.33" referred to above can be modified in one or more instances to be any other suitable ratio.

In an embodiment of the present disclosure, the tendon engagement structures 464 may comprise a pair of spaced apart spikes. In an embodiment of the present disclosure, the spikes may extend between about 30 to 100%, or about 40% of the distance between the bottom surface 456 to the free ends 460 of the legs 458 such that the engagement structures 464 do not extend below the free ends 460 of the legs 458. The distance from the top surface 454 to the distal ends of spike 464 may be about 0.3 to 1.0 of the length, $L_1$, and therefore may also be about 0.4 to 0.7 of the length, $L_1$, and therefore may also be about 0.5 to 0.7 of the length, $L_1$.

In an embodiment of the present disclosure, the engagement structures 464 may extend beyond the free ends 460 of the legs 458. For example, spikes may extend beyond the free ends 460 of the legs 460 such that they may engage or penetrate a bottom surface of a bore. The engagement structures 464 may be integrally formed in the implant 450. It will be appreciated that the engagement structures 464 may be integrally formed in the body member 452 such that they remain in a bore in a bone after surgery.

In an embodiment of the present disclosure, a length, $L_1$, between the top surface 454 and the free ends 460 of the legs 458 may be between about 5 millimeters and 12 millimeters. In an embodiment of the present disclosure, a length, $L_2$, of the legs 458 may be between about 2 millimeters and 7 millimeters. In an embodiment of the present disclosure, a length, $L_3$, between the legs 458, also referred to herein as a straddle, may be between about 3 millimeters and 8 millimeters. In an embodiment of the present disclosure, a length, $L_4$, of the body member 452 between the top surface 454 and the bottom surface 456 may be between about 2 millimeters and 7 millimeters. $L_4$ may also refer a length between the top surface 454 and a top surface of semi-circular gap 456, with the understanding that the semi-circular gap 456 may also be referred to as a concave gap. A width, $L_5$, of the body member 452 may be between about 5 and 9 millimeters or about 7 millimeters.

In an embodiment of the present disclosure, the ratio of $L_4$ and $L_1$ may be between about 0.15 to 0.5, or about 0.4. In an embodiment of the present disclosure, the ratio of $L_2$ and $L_1$ may be between about 0.3 to 0.7, or about 0.5. In an embodiment of the present disclosure, the ratio of $L_3$ and $L_1$ may be between about 0.5 to 0.9, or about 0.7.

Figure 20:
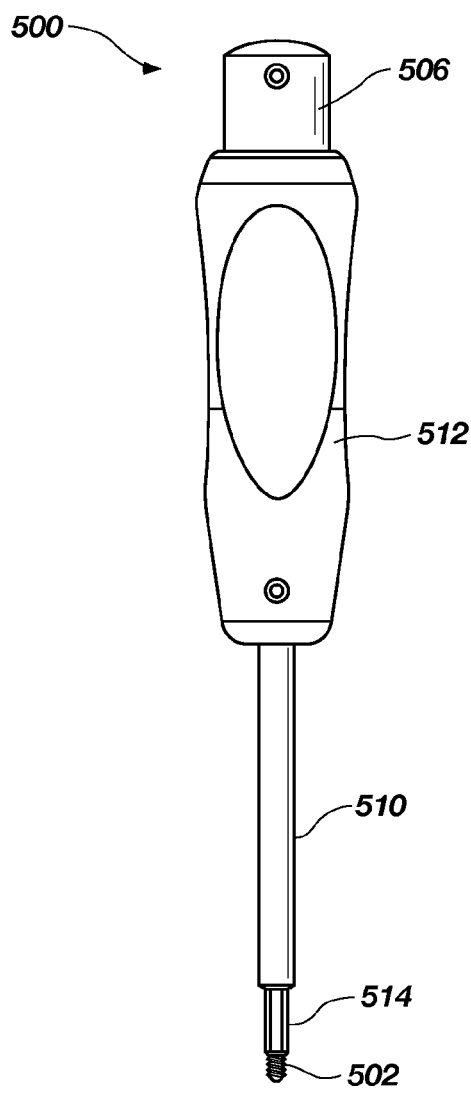
FIG. 20 is a side view of a drive tool for installing an implant and a fixation member pursuant to an embodiment of the present disclosure.
Figure 21:
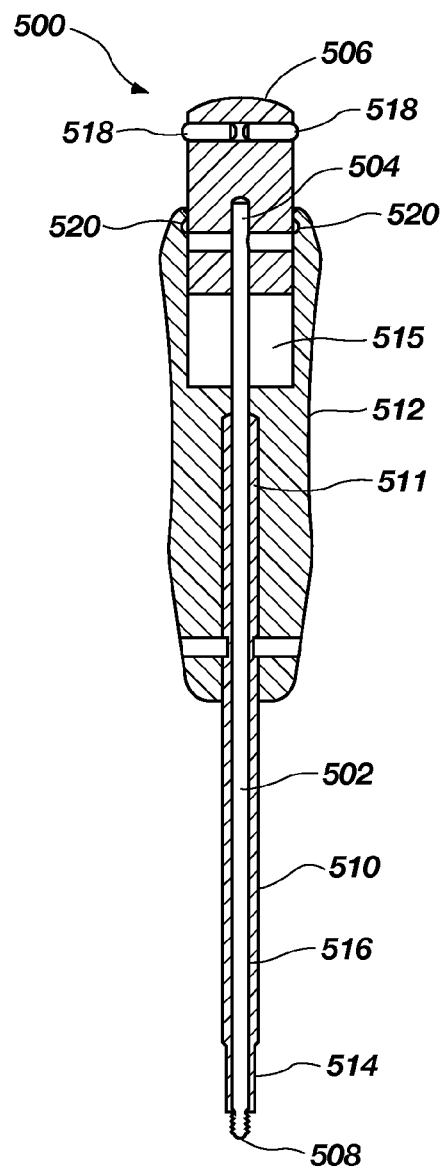
FIG. 21 is a cross-sectional view of the drive tool depicted in FIG. 20.

Referring now to FIGS. 20 and 21, there is depicted a tool or driver 500 for installing an implant and a fixation member pursuant to an embodiment of the present disclosure. The driver 500 may comprise a push rod 502. The push rod 502 may comprise a top end 504 connected to a handle 506. A bottom end 508 of the push rod 502 may include a mating member for affixing the rod 502 to an implant. In an embodiment of the present disclosure, the mating member may comprise a threaded shaft portion receivable in a threaded bore of an implant.

The driver 500 may further comprise a drive shaft 510. A top end 511 of the drive shaft 510 may be connected to a handle 512. A bottom end 514 of the drive shaft 510 may include a mating member for engaging a fixation member. In an embodiment of the present disclosure, the mating member may be configured to engage a socket of a fixation member or any other part of the fixation member.

The drive shaft 510 may include a hollow passageway 516. A portion of the push rod 502 may be disposed in the hollow passageway 516. The handle 512 may include a counterbore 515 for receiving the handle 506. It will be appreciated that the position of the push rod 502 and the drive shaft 510 may be variable with respect to each other. The push rod 502 and the drive shaft 510 may slide freely with respect to each other.

In particular, the push rod 502 may be extended and retracted from the free end of the drive shaft 510. The drive shaft 510 may rotate freely around the push rod 502. The drive shaft 510 and the push rod 502 may concentric. The position of the push rod 502 with respect to the shaft 510 may be fixed using a locking mechanism. For example, a suitable locking mechanism may include spring loaded ball detent 518 disposed in the handle 506. The detents 518 may engage a groove 520 formed in the counterbore 515.

Figure 18:
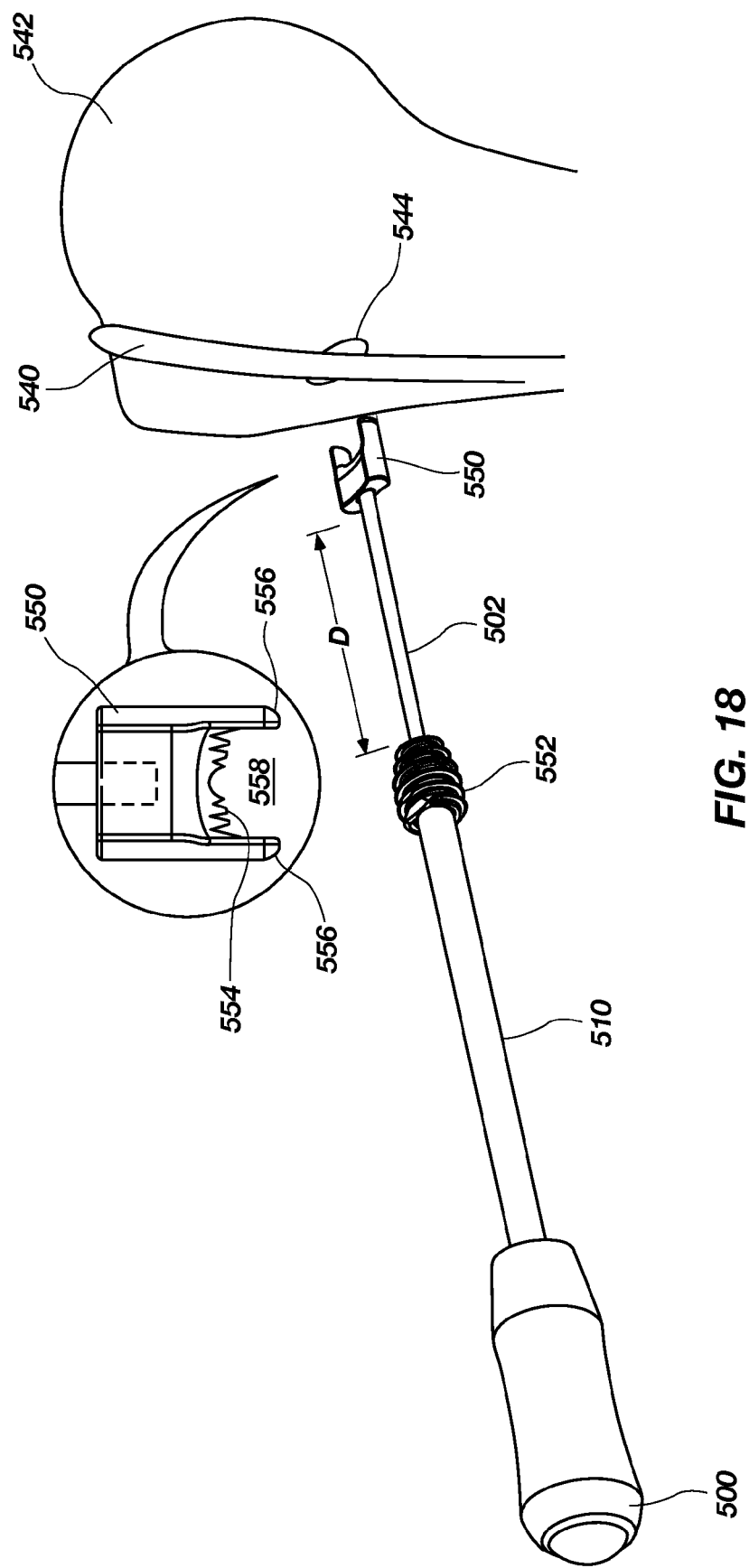
FIG. 18 is a perspective view of a head of a bone with a pre-drilled bore in relation to a drive tool for installing an implant and a fixation member into the bore.
Figure 19:
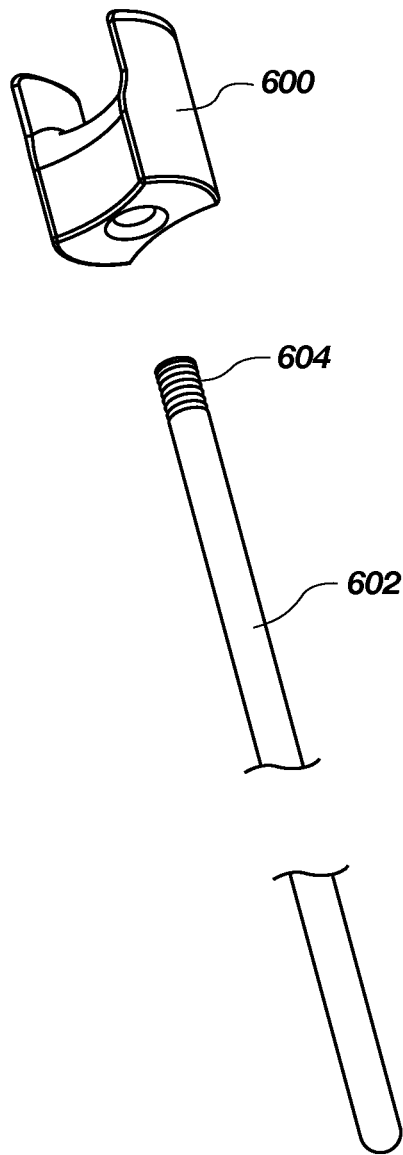
FIG. 19 is perspective view of an implant and a push rod.

Referring now to FIG. 18, there is depicted a method of anchoring a tendon 540 into a bore 544 formed in a bone 542. It is to be understood that tendon 540 may also be referred to herein as a flexible intracorporeal member, which may refer to an artificial or natural tendon or ligament, or other flexible intracorporeal member. A fixation member 552 may be installed onto the end of the drive shaft 510 of the drive 500. For example, an end of the drive shaft 510 may engage a socket in the fixation member 552. The push rod 502 may pass through a throughbore in the fixation member 552. An implant 550 may then be installed onto the end of the push rod 502. For example, the implant 550 may threadably engage an end of the push rod 502. The implant 550 may optionally comprise a plurality of tendon engaging members 554, such as teeth or spikes. The implant 550 may further include a pair of legs 556 forming a straddle 558. A distance, D, between the implant 550 and the fixation member 552 may be variable. When configured as shown in FIG. 18, the drive 500 may be utilized to anchor the tendon 540 in the bore 544 in the bone 542 using the same basic surgical techniques as shown in FIGS. 9-13. Referring now to FIG. 19, an implant 600 may also be installed on a threaded end 604 of a simple push rod 602.

For example, in an embodiment of the present disclosure, a method for securing a flexible intracorporeal member 540, such as an artificial or natural tendon or ligament, to the bone 542, may comprise:

selecting the drive shaft 510 having a fixation member 552 attached thereto;

selecting the push rod 502 having the implant 550 attached thereto;

placing the implant 550 into the bore 544 in the bone 542 and into contact with the flexible intracorporeal member 540, and holding said flexible intracorporeal member 540 against a defining surface of the bore 544 such as a bottom of the bore 544;

placing the fixation member 552 into the bore 544 in the bone 542, after the implant 550 is inside said bore 544, and securing the fixation member 552 to the bone 542 such that at least a portion of said fixation member 552 resides within the bore 544, to thereby block the implant 550 from exiting the bore 544 and hold the implant 550 against the flexible intracorporeal member 540;

detaching the push rod 502 from the implant 550;

detaching the drive shaft 510 from the fixation member 552;

removing the push rod 502 from the bore 544;

removing the drive shaft 510 from the bore 544.

In an embodiment of the present disclosure, instead of performing the steps of selecting the drive shaft 510 having a fixation member 552 attached thereto and selecting the push rod 502 having the implant 550 attached thereto, the method may comprise:

sliding the push rod 502 into the drive shaft 510;

attaching the fixation member 552 to the drive shaft 510; and attaching the implant 550 to the push rod 502.

Figure 22:
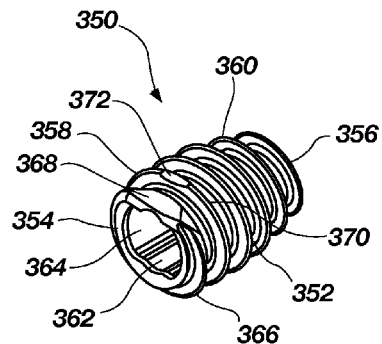
FIG. 22 is a perspective view of a fixation member pursuant to an embodiment of the present disclosure.
Figure 23:
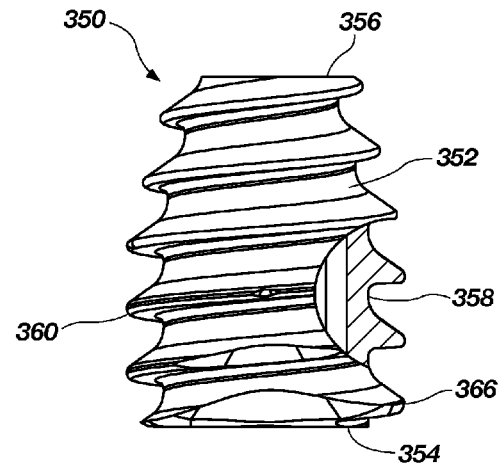
FIG. 23 is a partial, fragmentary side view of the fixation member depicted in FIG. 22.
Figure 24:
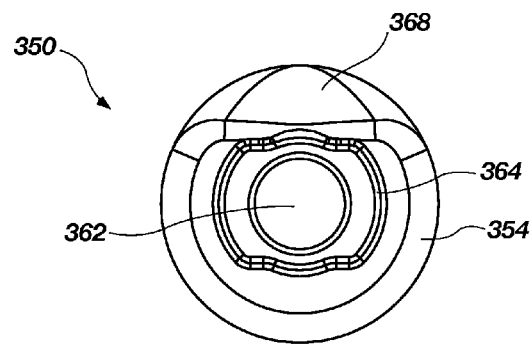
FIG. 24 is a top view of the fixation member depicted in FIG. 22.
Figure 26:
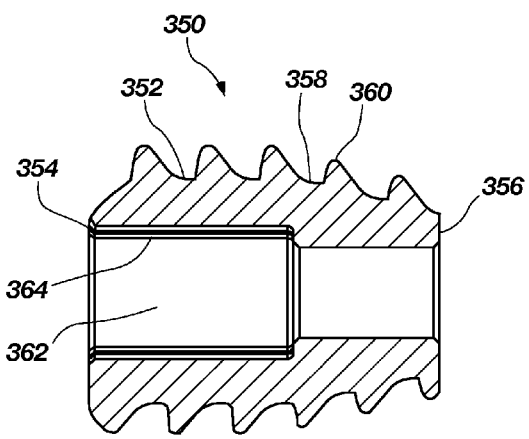
FIG. 26 is a cross-sectional view of the fixation member depicted in FIG. 22.
Figure 25:
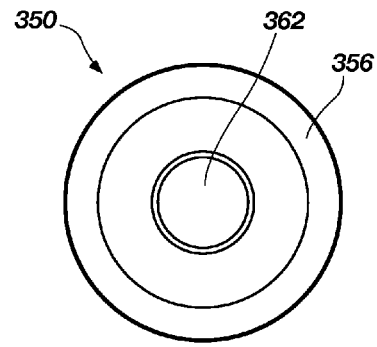
FIG. 25 is a bottom view of the fixation member depicted in FIG. 22.
Figure 27:
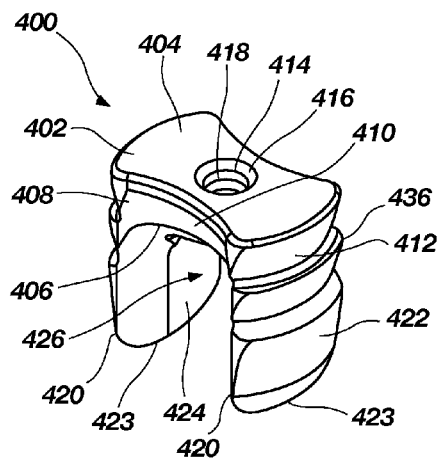
FIG. 27 is a perspective view of an implant pursuant to an embodiment of the present disclosure.

In an embodiment of the present disclosure, the above-described methods may further comprise:

the drive shaft 510 having a non-circular engaging portion 514 and wherein the fixation member 552 comprises an engaging surface defining a through bore 362 having a non-circular cross-sectional shape as shown most clearly in FIGS. 22 and 24, and wherein the step of attaching the fixation member 552 to the drive shaft 510 may further comprise sliding the non-circular engaging portion 514 of the drive shaft 510 into the non-circular portion of the through bore 362 of the fixation member 552, to thereby cause the engaging portion 514 of the drive shaft 510 to engage with the engaging surface of the fixation member 552, such that rotation of the fixation member 552 about an axis of rotation is confined to rotation with the drive shaft 510.

The non-circular engaging portion 514 may comprise any suitable non-circular cross-sectional shape. For example, the non-circular cross-sectional shape may comprise an octagon, a hexagon, a pentagon, a triangle, a square, a trapezoid, an ellipse, a rectangle, or any other non-circular shape.

Implants and fixation members according to the present disclosure may be formed from a wide range of materials, including, metal or plastic. In an embodiment of the present disclosure, the implant and the fixation member may be formed from a bio-compatible material, such as PEEK (polyether ether ketone).

In the foregoing Detailed Description, various features of the present disclosure are grouped together in a single embodiment for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description of the Disclosure by this reference, with each claim standing on its own as a separate embodiment of the present disclosure.

It is to be understood that the above-described arrangements are only illustrative of the application of the principles of the present disclosure. Numerous modifications and alternative arrangements may be devised by those skilled in the art without departing from the spirit and scope of the present disclosure and the appended claims are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of anchoring a tendon to a bone of a patient, the method comprising:
    forming a bore in the bone; and
    anchoring the tendon in the bore using an implant and a fixation member, wherein the implant is fixedly attached to an end of a push rod;
    wherein the implant includes a body member and a pair of legs, each of the pair of legs extending from the body member and terminating at a free end, the pair of legs defining a straddle for laterally confining the tendon within the bore;
    wherein the implant is disposed in the bore between the fixation member and a bottom surface of the bore;
    wherein the implant comprises a substantially planar top surface formed on the body member opposite the pair of legs, the top surface comprising a pair of oppositely disposed, concave edges and a pair of oppositely disposed, convex edges;
    wherein a length of the concave edges of the top surface are greater than a length of the convex edges of the top surface.

2. The method of claim 1, wherein the body member further comprises a pair of sidewall relief channels, each of the sidewall relief channels extending from the top surface of the body member to the straddle.

3. The method of claim 2, wherein each of the sidewall relief channels comprises a concave surface.

4. The method of claim 3, wherein the body member further comprises a pair of convex sidewall portions.

5. The method of claim 2, wherein the sidewall relief channels are disposed on opposing sides of the body member.

6. The method of claim 1, wherein the implant further comprises one or more bone engagement structures.

7. The method of claim 6, wherein the bone engagement structures comprise barbs.

8. The method of claim 1, wherein the implant is characterized by a lack of any bone engagement structures.

9. The method of claim 1, wherein the implant further comprises one or more tendon engagement members.

10. The method of claim 9, wherein the one or more tendon engagement members extend from a lower surface of the body member.

11. The method of claim 9, wherein the one or more tendon engagement members comprise teeth members.

12. The method of claim 1, wherein the implant comprises a mating member configured and adapted for removably attaching the implant the end of the push rod.

13. The method of claim 12, wherein the mating member comprises a bore formed in a surface of the body member.

14. The method of claim 13, wherein the bore formed in the surface of the body member comprises a threaded sidewall for threadably engaging the end of the push rod.

15. The method of claim 12, wherein the mating member comprises a socket.

16. The method of claim 1, wherein the fixation member comprises a proximal end and a distal end, and wherein the top surface of the implant is configured and adapted for engaging the distal end of the fixation member.

17. The method of claim 1, wherein the implant further comprises a pair of oppositely disposed, convex sidewalls, each of the convex sidewalls extending between one of the convex edges of the top surface and the free end of one of the pair of legs, wherein each of the convex sidewalls comprises a proximal to distal taper.

18. The method of claim 1, wherein the fixation member comprises bone engagement structure.

19. The method of claim 18, wherein the bone engagement structure of the fixation member comprises one of threads and barbs.

20. The method of claim 1, wherein the fixation member comprises an elongate body having a threaded outer surface.

21. The method of claim 20, wherein the elongate body further comprises a proximal end and a distal end, and wherein a throughbore extends from the proximal end to the distal end.

22. The method of claim 21, wherein the fixation member further comprises a socket for engaging an end of a drive shaft.

23. The method of claim 1, wherein the free end of each of the pair of legs is contoured to conform to a contour of a bottom surface of the bore in the bone.

24. The method of claim 1, wherein the implant and the fixation member are not integrally connected.

25. The method of claim 1, further comprising a suture anchor extending from a top surface of the fixation member, said suture anchoring comprising a loop.

26. The method of claim 1, wherein the body member further comprises a bottom surface, wherein a ratio of a length between the top surface and the bottom surface and a length between the top surface and the free end of a leg is about 0.15 to 0.5.

27. The method of claim 1, wherein the body member further comprises a top surface and a bottom surface, wherein a ratio of a length between the top surface and the bottom surface and a length between the top surface and the free end of a leg is about 0.4.

28. The method of claim 1, wherein the body member further comprises a bottom surface, wherein at least one spike extends from the bottom surface, said at least one spike being integrally connected to the body member.

29. The method of claim 28, wherein the at least one spike comprises a pair of spaced apart spikes extending parallel to, and between the pair of legs, wherein a distance between the pair of legs is $L_3$, wherein a lateral distance between a first leg and a first spike is about 0.33 of $L_3$, wherein a lateral distance between the first spike and the second spike is about 0.33 of $L_3$, and wherein a lateral distance between the second spike and a second leg is about 0.33 of $L_3$.

30. The method of claim 28, wherein the at least one spike extends between about 30 to 100% of a distance between the bottom surface and the free ends of the legs.

31. The method of claim 28, wherein the at least one spike extends beyond the free ends of the legs.

32. A method of anchoring a tendon to a bone of a patient, the method comprising:
forming a bore in the bone; and
anchoring the tendon in the bore using an implant and a fixation member, wherein the implant is fixedly attached to an end of a push rod;
wherein the implant includes a body member and a pair of legs, each of the pair of legs extending from the body member and terminating at a free end, the pair of legs defining a straddle for laterally confining the tendon within the bore;
wherein the implant is disposed in the bore between the fixation member and a bottom surface of the bore;
wherein the implant comprises a substantially planar top surface formed on the body member opposite the pair of legs, the top surface comprising a pair of oppositely disposed, concave edges and a pair of oppositely disposed, convex edges;
wherein the implant comprises a pair of oppositely disposed, concave walls extending downwardly from the concave edges and a pair of oppositely disposed convex walls extending downwardly from the convex edges, wherein the convex sidewalls are narrower than the concave sidewalls.

33. The method of claim 32, wherein the body member further comprises a pair of sidewall relief channels, each of the sidewall relief channels extending from the top surface of the body member to the straddle.

34. The method of claim 33, wherein each of the sidewall relief channels comprises a concave surface.

35. The method of claim 34, wherein the body member further comprises a pair of convex sidewall portions.

36. The method of claim 33, wherein the sidewall relief channels are disposed on opposing sides of the body member.

37. The method of claim 32, wherein the implant further comprises one or more bone engagement structures.

38. The method of claim 37, wherein the bone engagement structures comprise barbs.

39. The method of claim 32, wherein the implant is characterized by a lack of any bone engagement structures.

40. The method of claim 32, wherein the implant further comprises one or more tendon engagement members.

41. The method of claim 40, wherein the one or more tendon engagement members extend from a lower surface of the body member.

42. The method of claim 40, wherein the one or more tendon engagement members comprise teeth members.

43. The method of claim 32, wherein the implant comprises a mating member configured and adapted for removably attaching the implant the end of the push rod.

44. The method of claim 43, wherein the mating member comprises a bore formed in a surface of the body member.

45. The method of claim 44, wherein the bore formed in the surface of the body member comprises a threaded sidewall for threadably engaging the end of the push rod.

46. The method of claim 43, wherein the mating member comprises a socket.

47. The method of claim 32, wherein the fixation member comprises a proximal end and a distal end, and wherein the top surface of the implant is configured and adapted for engaging the distal end of the fixation member.

48. The method of claim 32, wherein the implant further comprises a pair of oppositely disposed, convex sidewalls, each of the convex sidewalls extending between one of the convex edges of the top surface and the free end of one of the pair of legs, wherein each of the convex sidewalls comprises a proximal to distal taper.

49. The method of claim 32, wherein the fixation member comprises bone engagement structure.

50. The method of claim 49, wherein the bone engagement structure of the fixation member comprises one of threads and barbs.

51. The method of claim 32, wherein the fixation member comprises an elongate body having a threaded outer surface.

52. The method of claim 51, wherein the elongate body further comprises a proximal end and a distal end, and wherein a throughbore extends from the proximal end to the distal end.

53. The method of claim 52, wherein the fixation member further comprises a socket for engaging an end of a drive shaft.

54. The method of claim 32, wherein the free end of each of the pair of legs is contoured to conform to a contour of a bottom surface of the bore in the bone.

55. The method of claim 32, wherein the implant and the fixation member are not integrally connected.

56. The method of claim 32, further comprising a suture anchor extending from a top surface of the fixation member, said suture anchoring comprising a loop.

57. The method of claim 32, wherein the body member further comprises a bottom surface, wherein a ratio of a length between the top surface and the bottom surface and a length between the top surface and the free end of a leg is about 0.15 to 0.5.

58. The method of claim 32, wherein the body member further comprises a top surface and a bottom surface, wherein a ratio of a length between the top surface and the bottom surface and a length between the top surface and the free end of a leg is about 0.4.

59. The method of claim 32, wherein the body member further comprises a bottom surface, wherein at least one spike extends from the bottom surface, said at least one spike being integrally connected to the body member.

60. The method of claim 59, wherein the at least one spike comprises a pair of spaced apart spikes extending parallel to, and between the pair of legs, wherein a distance between the pair of legs is $L_3$, wherein a lateral distance between a first leg and a first spike is about 0.33 of $L_3$, wherein a lateral distance between the first spike and the second spike is about 0.33 of $L_3$, and wherein a lateral distance between the second spike and a second leg is about 0.33 of $L_3$.

61. The method of claim 59, wherein the at least one spike extends between about 30 to 100% of a distance between the bottom surface and the free ends of the legs.

62. The method of claim 59, wherein the at least one spike extends beyond the free ends of the legs.

* * * * *